(12) United States Patent
Bochenko et al.

(10) Patent No.: US 8,328,082 B1
(45) Date of Patent: Dec. 11, 2012

(54) MEDICATION CONTAINER ENCODING, VERIFICATION, AND IDENTIFICATION

(75) Inventors: Walter John Bochenko, Encinitas, CA (US); Mark VanVeen, Cardiff, CA (US); Stephen Michael Prince, La Jolla, CA (US)

(73) Assignee: CRISI Medical Systems, Inc., San Diego, CA (US)

( * ) Notice: Subject to any disclaimer, the term of this patent is extended or adjusted under 35 U.S.C. 154(b) by 0 days.

(21) Appl. No.: 13/149,782

(22) Filed: May 31, 2011

Related U.S. Application Data

(60) Provisional application No. 61/349,878, filed on May 30, 2010.

(51) Int. Cl.
| | |
|---|---|
| *G06K 7/10* | (2006.01) |
| *G06K 7/00* | (2006.01) |
| *G06K 7/14* | (2006.01) |
| *G06K 17/00* | (2006.01) |
| *G06F 19/00* | (2006.01) |
| *A61M 31/00* | (2006.01) |

(52) U.S. Cl. .................... 235/375; 235/462.01; 235/435; 235/454; 235/462.15; 604/67

(58) Field of Classification Search .................... 604/67; 235/462.01, 375, 435, 454, 462.15; 600/423, 600/427, 432, 433
See application file for complete search history.

(56) References Cited

U.S. PATENT DOCUMENTS

| | | | |
|---|---|---|---|
| 4,650,475 A |  | 3/1987 | Smith et al. |
| 4,853,521 A | * | 8/1989 | Claeys et al. .................. 235/375 |
| 4,978,335 A | * | 12/1990 | Arthur, III ........................ 604/67 |
| 5,011,032 A | * | 4/1991 | Rollman ........................ 215/230 |
| 5,078,683 A | * | 1/1992 | Sancoff et al. .................. 604/67 |
| 5,279,576 A |  | 1/1994 | Loo et al. |
| 5,383,858 A | * | 1/1995 | Reilly et al. .................. 604/152 |
| 5,628,309 A |  | 5/1997 | Brown |
| 5,651,775 A |  | 7/1997 | Walker et al. |
| 5,692,640 A |  | 12/1997 | Caulfield et al. |
| 5,782,814 A |  | 7/1998 | Brown et al. |
| 5,792,117 A |  | 8/1998 | Brown |
| 5,873,731 A |  | 2/1999 | Prendergast |
| 5,984,901 A |  | 11/1999 | Sudo et al. |
| 6,019,745 A |  | 2/2000 | Gray |
| 6,123,686 A |  | 9/2000 | Olsen et al. |
| 6,192,945 B1 | * | 2/2001 | Ford et al. ......................... 141/2 |
| 6,338,200 B1 |  | 1/2002 | Baxa et al. |

(Continued)

FOREIGN PATENT DOCUMENTS

DE      29617777 U1    12/1996

OTHER PUBLICATIONS

International Search Report dated Aug. 2, 2011 for corresponding PCT Application No. PCT/US2010/055322.

*Primary Examiner* — Daniel Walsh

(74) *Attorney, Agent, or Firm* — Mintz, Levin, Cohn, Ferris, Glovsky and Popeo, P.C.

(57) ABSTRACT

A medication container encoding, verification and identification method is provided that includes receiving data characterizing a medication, generating an identifier encapsulating the data and applying an identifier to a medication container such that it is automatically readable by a medication administration device and/or a medication wasting device. Related apparatus, systems, methods and articles are also described.

19 Claims, 12 Drawing Sheets

U.S. PATENT DOCUMENTS

| | | | |
|---|---|---|---|
| 6,468,424 B1* | 10/2002 | Donig et al. | 210/232 |
| RE38,189 E | 7/2003 | Walker et al. | |
| 6,626,862 B1* | 9/2003 | Duchon et al. | 604/110 |
| D481,121 S | 10/2003 | Evans | |
| D485,356 S | 1/2004 | Evans | |
| 6,685,678 B2 | 2/2004 | Evans et al. | |
| 6,790,198 B1 | 9/2004 | White et al. | |
| 6,960,192 B1 | 11/2005 | Flaherty et al. | |
| 7,017,623 B2* | 3/2006 | Tribble et al. | 141/27 |
| 7,074,209 B2 | 7/2006 | Evans et al. | |
| 7,115,113 B2 | 10/2006 | Evans et al. | |
| 7,117,041 B2 | 10/2006 | Engleson et al. | |
| 7,161,488 B2 | 1/2007 | Frasch | |
| 7,236,936 B2* | 6/2007 | White et al. | 705/3 |
| 7,470,266 B2* | 12/2008 | Massengale et al. | 604/890.1 |
| 7,722,083 B2 | 5/2010 | McCarthy et al. | |
| 7,727,196 B2 | 6/2010 | Neer | |
| 7,834,816 B2* | 11/2010 | Marino et al. | 343/867 |
| 7,976,508 B2* | 7/2011 | Hoag | 604/189 |
| 7,991,627 B2 | 8/2011 | Hutchinson et al. | |
| 8,035,517 B2 | 10/2011 | Gibson | |
| 8,151,835 B2* | 4/2012 | Khan et al. | 141/114 |
| 2002/0040208 A1* | 4/2002 | Flaherty et al. | 604/288.01 |
| 2002/0088131 A1* | 7/2002 | Baxa et al. | 33/494 |
| 2002/0098598 A1* | 7/2002 | Coffen et al. | 436/536 |
| 2002/0099334 A1 | 7/2002 | Hanson et al. | |
| 2002/0177811 A1* | 11/2002 | Reilly et al. | 604/152 |
| 2002/0188259 A1 | 12/2002 | Hickle et al. | |
| 2003/0012701 A1* | 1/2003 | Sangha et al. | 422/102 |
| 2003/0052787 A1 | 3/2003 | Zerhusen et al. | |
| 2003/0055685 A1* | 3/2003 | Cobb et al. | 705/3 |
| 2003/0065537 A1 | 4/2003 | Evans | |
| 2003/0088238 A1 | 5/2003 | Poulsen et al. | |
| 2003/0135388 A1* | 7/2003 | Martucci et al. | 705/2 |
| 2003/0139701 A1* | 7/2003 | White et al. | 604/67 |
| 2003/0139706 A1* | 7/2003 | Gray | 604/199 |
| 2003/0140929 A1 | 7/2003 | Wilkes et al. | |
| 2003/0174326 A1* | 9/2003 | Rzasa et al. | 356/326 |
| 2004/0051368 A1* | 3/2004 | Caputo et al. | 299/1.9 |
| 2004/0082918 A1 | 4/2004 | Evans et al. | |
| 2004/0092885 A1* | 5/2004 | Duchon et al. | 604/246 |
| 2004/0104271 A1* | 6/2004 | Martucci et al. | 235/472.01 |
| 2004/0186437 A1 | 9/2004 | Frenette et al. | |
| 2004/0204673 A1 | 10/2004 | Flaherty | |
| 2005/0101905 A1* | 5/2005 | Merry | 604/19 |
| 2005/0106225 A1* | 5/2005 | Massengale et al. | 424/448 |
| 2005/0107923 A1* | 5/2005 | Vanderveen | 700/282 |
| 2005/0182358 A1 | 8/2005 | Veit et al. | |
| 2005/0277890 A1 | 12/2005 | Stewart et al. | |
| 2006/0079767 A1* | 4/2006 | Gibbs et al. | 600/432 |
| 2006/0079843 A1 | 4/2006 | Brooks et al. | |
| 2006/0116639 A1* | 6/2006 | Russell | 604/131 |
| 2006/0122577 A1 | 6/2006 | Poulsen et al. | |
| 2006/0144942 A1* | 7/2006 | Evans et al. | 235/435 |
| 2006/0226089 A1* | 10/2006 | Robinson et al. | 210/787 |
| 2006/0229551 A1* | 10/2006 | Martinez et al. | 604/67 |
| 2006/0258985 A1* | 11/2006 | Russell | 604/151 |
| 2006/0265186 A1* | 11/2006 | Holland et al. | 702/182 |
| 2007/0043335 A1 | 2/2007 | Olsen et al. | |
| 2007/0135765 A1* | 6/2007 | Miller et al. | 604/131 |
| 2007/0136218 A1* | 6/2007 | Bauer et al. | 706/12 |
| 2007/0166198 A1* | 7/2007 | Sangha et al. | 422/99 |
| 2007/0167919 A1* | 7/2007 | Nemoto et al. | 604/189 |
| 2007/0191787 A1* | 8/2007 | Lim et al. | 604/246 |
| 2007/0279625 A1* | 12/2007 | Rzasa et al. | 356/300 |
| 2007/0299421 A1 | 12/2007 | Gibson | |
| 2008/0045930 A1 | 2/2008 | Makin et al. | |
| 2008/0051937 A1* | 2/2008 | Khan et al. | 700/240 |
| 2008/0061153 A1 | 3/2008 | Hickle et al. | |
| 2008/0125724 A1 | 5/2008 | Monroe | |
| 2008/0191013 A1* | 8/2008 | Liberatore | 235/385 |
| 2008/0208042 A1 | 8/2008 | Ortenzi et al. | |
| 2008/0234630 A1 | 9/2008 | Iddan et al. | |
| 2008/0243088 A1* | 10/2008 | Evans | 604/246 |
| 2008/0294108 A1* | 11/2008 | Briones et al. | 604/131 |
| 2009/0018494 A1 | 1/2009 | Nemoto et al. | |
| 2009/0030730 A1* | 1/2009 | Dullemen et al. | 705/3 |
| 2009/0036846 A1* | 2/2009 | Dacquay et al. | 604/290 |
| 2009/0043253 A1* | 2/2009 | Podaima | 604/67 |
| 2009/0069714 A1 | 3/2009 | Eichmann et al. | |
| 2009/0149744 A1* | 6/2009 | Nemoto et al. | 600/432 |
| 2009/0157008 A1* | 6/2009 | Vitral | 604/187 |
| 2009/0159654 A1 | 6/2009 | Grimard | |
| 2009/0294521 A1* | 12/2009 | de La Huerga | 235/375 |
| 2010/0065643 A1* | 3/2010 | Leyvraz et al. | 235/470 |
| 2010/0152562 A1* | 6/2010 | Goodnow et al. | 600/347 |
| 2010/0153136 A1* | 6/2010 | Whittacre et al. | 705/3 |
| 2010/0174266 A1 | 7/2010 | Estes | |
| 2010/0262002 A1* | 10/2010 | Martz | 600/432 |
| 2010/0280486 A1* | 11/2010 | Khair et al. | 604/506 |
| 2010/0305499 A1 | 12/2010 | Matsiev et al. | |
| 2011/0060198 A1 | 3/2011 | Bennett et al. | |
| 2011/0111794 A1 | 5/2011 | Bochenko et al. | |
| 2011/0112473 A1* | 5/2011 | Bochenko et al. | 604/68 |
| 2011/0112474 A1* | 5/2011 | Bochenko et al. | 604/68 |
| 2011/0220713 A1* | 9/2011 | Cloninger | 235/375 |
| 2011/0224649 A1* | 9/2011 | Duane et al. | 604/523 |
| 2011/0264069 A1* | 10/2011 | Bochenko | 604/404 |
| 2012/0037266 A1* | 2/2012 | Bochenko | 141/1 |
| 2012/0041355 A1 | 2/2012 | Edman et al. | |

\* cited by examiner

MEDICATION CONTAINER ENCODING, VERIFICATION, AND IDENTIFICATION

RELATED APPLICATION

This application claims priority to U.S. Pat. App. Ser. No. 61/349,878 filed on May 30, 2010 and entitled: "Medication Identification Encoding and Verification", the contents of which are hereby incorporated by reference.

FIELD

The subject matter described herein relates to a medication identification, encoding and verification for use in scanning, verifying and/or marking medication containers so the medications in those containers can be properly identified and documented during the process of patient medication preparation, administration, and disposal. Medication containers can include syringes, bags, vials, medication transfer apparatus as well as medical packaging with marking applied during various manufacturing and pharmacy processes.

BACKGROUND

Many health care procedures involving the preparation, administration and wasting of medication involve a clinician manually reading labeling applied to various medication containers. Such an arrangement is fraught for user error resulting in over-medication, under-medication, administration of non-compatible medications and/or administration of medications to which a patient is allergic. In addition, problems also arise in properly labeling medication containers during manufacture and preparation (whether in the pharmacy or otherwise). Proper labeling is of particular import when there are multiple components bundled together.

SUMMARY

In one aspect, data characterizing medication within a medication container is received. Thereafter, an identifier encapsulating data characterizing the medication is generated and applied to the medication container. The identifier can be positioned such that it is automatically readable by a medication administration device when the medication is administered to a patient and/or by a medication disposal device when the medication is wasted.

The medication container can take a variety of forms. The medication container can be a syringe comprising a barrel portion and a tip portion comprising a fluid outlet such that the identifier is applied to the tip portion. The tip portion can comprise a cylindrical or conical outer surface terminating at the fluid outlet such that the identifier is applied to the outer surface. The tip portion can comprise a Luer lock fitting such that identifier is positioned on the Luer lock fitting.

The medication container can be a vial having a stopper or a corresponding stopper closure to which the identifier is applied. The medication container can be a medication bag containing a medication solution having a Luer fitting and/or a spikeable port to which the identifier is applied. The medication container can be an envelope having a Luer fitting or a tubing set extending therefrom to which the identifier is applied. The medication container can comprise a fluid transfer device for transferring the medication from a first receptacle to a second receptacle. The medication container can comprise packaging including a medication receptacle containing the medication. The medication container can be a fluid tubing set having a fluid outlet such as a Luer fitting to which the identifier is applied.

The medication administration device can take a variety of forms. For example, the medication administration device can comprise: a housing, a medication port accessible via an outer surface of the housing, an identification sensor disposed within the housing to generate information indicative of contents of the medication container when the fluid outlet of the medication container is fluidically coupled to the medication port, and a transmitter disposed within the housing and in communication with the identification sensor to transmit the information generated by the identification sensor to a remote data collection system.

The encapsulated data can comprise a reference to data accessible via a communications network. In such cases, the encapsulated data can include a a Uniform Resource Locator, a database path, a pointer to a look-up table, or a file path such that the medication administration device accesses such remote information (which can be used, for example, for more informed patient treatment, etc.). In addition or in the alternative, the medication administration device can comprises a memory storing data corresponding to the encapsulated data which is accessed when the medication administration device reads the identifier.

The encapsulated data can be formatted using an industry standard representation of the medication being characterized or a proprietary representation of the medication being characterized. The referenced data accessible via a communications network can include one or more of: an NDC code (National Drug Code), a segment of the NDC code identifying the drug product, a segment of the NDC code identifying the drug package, a unique identifier code, a human readable alphanumeric, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date. The encapsulated data can additionally or alternatively also include such information.

The identifier can take a variety of forms. For example, the identifier can be any of: optical identifiers, magnetic identifiers, RFID identifiers, and mechanically encoded identifiers. The identifier can be etched on an outer surface of the medication container. The identifier can be a mechanical element secured to or extending from the medication container. The identifier can include a coded disc or coded ring secured to the medication container.

The medication container can be bundled with at least one other item (e.g., second medication container, fluid adapter, tubing set, packaging, etc.) bearing a second identifier corresponding to the identifier. In such cases, it can be verified, after the bundling, that the identifier on the medication container corresponds to the second identifier on the at least one other item.

In a further aspect, data is read from a medication source characterizing medication contained by the medication source. Thereafter, an identifier encapsulating data characterizing the medication is generated and is applied to a medication container filled or to be filled with the medication from the medication source. The identifier can be positioned such that it is readable by a medication administration device when administering the medication to a patient or when disposing the medication without deliberate effort on behalf of a clinician to facilitate information transfer between the medication container and the medication administration device or the medication wasting device.

In a further aspect, a medication identification encoding and verification apparatus is provided that includes a medication information source, an identification information reader (ID reader), an identification information writer (ID writer), a verification method to check the read information and a medication identification target (ID target). The ID reader includes a detector, scanner or imaging element to receive the medication identification information. The ID writer includes a marking element to deposit or encode identification information onto the ID target. The ID target receives the encoded identification information mark, image, code or other information rich media content. If the medication container is a syringe, the encoded information on the target is positioned such that it can be read by a medication administration device when administering the medication to a patient without deliberate effort on behalf of a clinician to facilitate information transfer between the medication container and the medication administration device.

In another aspect, a medication identification encoding and verification apparatus is provided with a second ID reader, a verification comparator, an identification information verification writer (IDV writer) and a second identification information target on packaging materials. The second ID reader includes a scanner element to receive medication information from a medication container or associated medical packaging. The verification comparator includes means for comparing desired identification information to medication container identification information. The IDV writer includes a marking element to deposit or encode identification information on a second ID target. The second ID target receives the second identification information mark. The second ID target can be packaging material. A read-write instrument can be provided for reading a medication identification code source and writing information to a target for encoding the target with the medication identification information used, for example, in a pharmaceutical manufacturing facility. In a further variation that can be used in a pharmaceutical repacking operation or in-hospital pharmacy, the reader can identify medication information from a multi-dose container and the writer can then encode single or partial dose information on the target. In this variation, the written information can be different from the original read information in that it can indicate smaller volumes, lower concentrations or be a patient specific dose. Multiple writes can be made on multiple targets to encode information about aliquots of medication written onto multiple single dose containers.

The information reader aspect of the read-write instrument can be any one of a linear bar-code reader, a 2D barcode reader, a magnetic strip reader, an image capture device, a camera, a manual data input information string, a stored alpha numeric character string, a unique symbolic identifier.

The information writer aspect of the read-write instrument can be any one of a laser, a printer, a hot stamp, a magnetic coding element, an electronic coding element, an RFID writer, a printed label, a coded disc, or coded ring element to be affixed to a medication container or packaging.

The information target can be any one of a syringe including but not limited to an empty and/or a prefilled syringe, a bag, a vial, a medication transfer apparatus including but not limited to an fluid administration set, a vial transfer apparatus, packaging, a medication container ID label marking element or coded disc, or coded ring to be affixed to the medication container. The information element can be applied to the tip portion (i.e., the portion of the medication container having the fluid outlet and a diameter smaller than or equal to the chamber of the medication container, etc.) or fluid outlet of the medication container.

The medication container and or the vial transfer apparatus can be enveloped in a sterile pouch (i.e., enclosure, etc.). The sterile pouch can contain information indicative of the encoded information on the information transfer element. The medication information transfer element can be part of a kit that also contains the vial and medication instructions for use. The kit can be manufactured complete by a pharmaceutical company including the medication in the vial and the information transfer apparatus. The kit can be packaged by a local pharmacy, a pharmaceutical repackaging operation or an in-hospital pharmacy and can include a pharmaceutical company packaged vial and the information applied to a fluid transfer apparatus.

In the pharmacy and/or pharmaceutical repackaging kit configuration the pharmacy can match and verify the medication information on the vial and vial packaging with the medication information on the transfer apparatus packaging and the information transfer element. The encoded information on the transfer apparatus can be positioned such that it can be read by a medication administration device when administering the medication to a patient without deliberate effort on behalf of a clinician to facilitate information transfer between the medication container and the medication administration device. Once matched and verified the pharmacy can join the vial and information transfer apparatus into a secondary package and label the kit. The secondary package can provide a tamper evident element providing assurance of maintaining the matched elements. The secondary package can contain pharmacy specific information including lot number, packaging date, medication expiration date, dosage, patient information and/or container serial number.

In a pharmacy and/or pharmaceutical repackaging operation, the read-write instrument can be provided for reading a medication identification code source and writing information to multiple targets with the medication identification information encoded on multiple medication containers. In this variation, a multi-dose medication container (vial, Act-O-Vial™, bag, bottle, ampoule, syringe, etc.) is provided to the pharmaceutical filler. Using the method, the pharmaceutical filler can encode multiple containers, or transfer elements, sub-dividing the contents of a multi-dose container into more than one dose administration sub-container. The multi-dose container information can be read and verified with an identification code. Then multiple sub-containers can be written (encoded) with sub-container information. The written sub-container information can contain the same or different information than the multi-dose medication container. The sub-container information can include any information useful for characterizing the contents of the sub-container (such as the data described above). If the sub-container is a syringe, the encoded information on the target can be positioned such that it can be read by a medication administration device when administering the medication to a patient without deliberate effort on behalf of a clinician to facilitate information transfer between the medication container and the medication administration device.

The encoded information can be selected from a group comprising: optically encoded information, optical image information, magnetically encoded information, radio frequency detectable information, and mechanically detectable information. The encoded information can include a unique identifier, NDC information, dose, concentration, package serial number, lot number, expiration date. The encoded information can be based on an industry standard representation of information content or a proprietary representation of the content.

The current subject matter provides many advantages. For example, by allowing for the automatic identification of the contents of medication containers (whether during administration of such medication or as part of a verification process during manufacture/preparation), medication administration errors can be greatly reduced. In addition, adverse effects from drug allergies and incompatible medications can be significantly minimized by providing a medication container that can be automatically identified. Providing a medication container labeled in a way that is automatically readable by a medication administration device without deliberate effort on the part of the clinician, greatly reduces the possibility of human error or that the label identification step will be skipped or adversely abbreviated in an effort to focus on immediate patient care needs. Lastly, proper record keeping can be maintained with regard to wasted medication (which is especially important with regard to controlled substances).

The details of one or more variations of the subject matter described herein are set forth in the accompanying drawings and the description below. Other features and advantages of the subject matter described herein will be apparent from the description and drawings, and from the claims.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings.

Like reference symbols in the various drawings indicate like or similar elements.

DETAILED DESCRIPTION

Figure 1A:
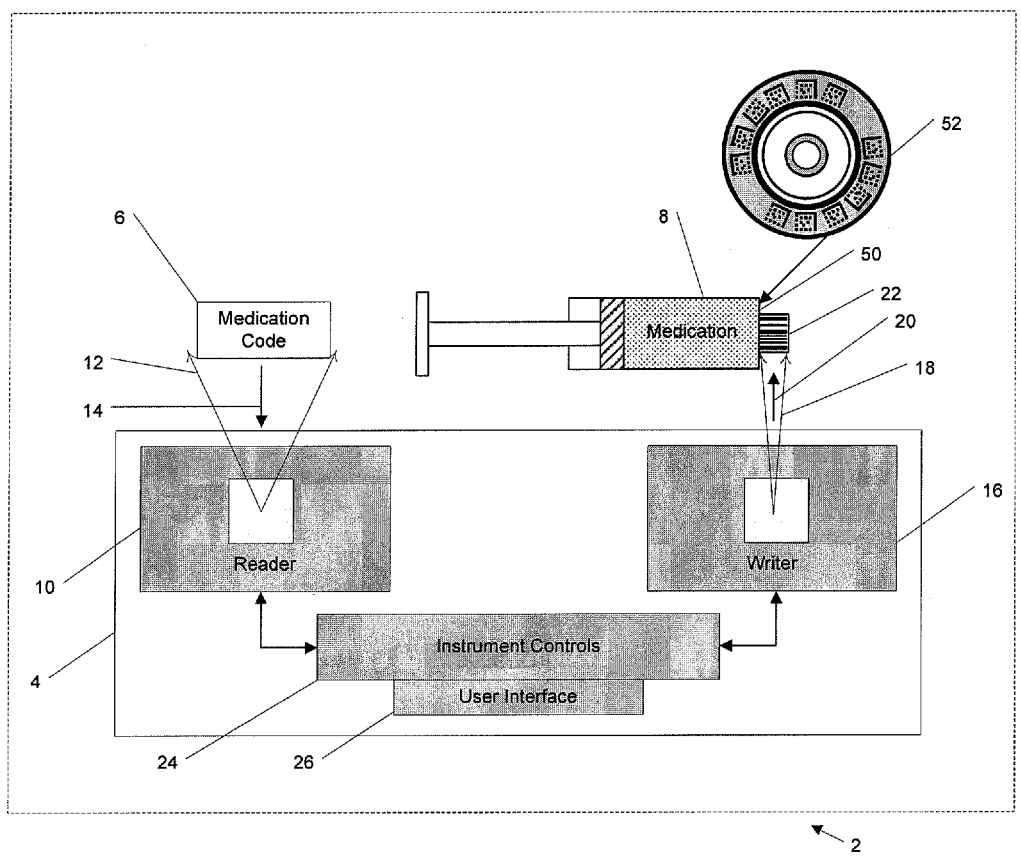
FIG. 1A is a diagram illustrating a medication identification information read and write apparatus for use with a syringe container.

FIG. 1A is a diagram illustrating a medication identification information read and write apparatus 2 that can be used to implement a medication container encoding and identification method. Apparatus 2 can include a read-write instrument 4 that can include one or more information readers 10, an information writer 16 and an information target 8. With such an arrangement, an entity or device such as a pharmaceutical manufacturer, a pharmaceutical repackager, a local pharmacy or an in-hospital pharmacy can access or read medication identification information 14 from medication code source 6. This read medication identification information 14 can be subsequently written, applied (e.g., deposited, encoded, etc.) in the form of medication identification information 20 onto or into information target 8 for the purpose of encoding target 8 at the fluid outlet. The encoded medication identification information on the target (sometimes referred to herein as an "identifier") can be positioned such that it can be read by a medication administration device when administering the medication to a patient without deliberate effort on behalf of a clinician to facilitate information transfer between the medication container and the medication administration device. This is further described below in connection with FIG. 10.

The medication identification information 20 can be displayed on a variety of locations on an information target 8 (i.e., a medication container, etc.). For example, when the information target 8, the medication identification information 20 can be positioned on a tip of the syringe. More specifically, in some implementations, the medication identification information 20 can be placed on a tapered portion of the tip, a Luer lock fitting on the tip, and a portion of the tip interposed between the tapered portion and the cylindrical chamber of the syringe.

The current subject matter is applicable to a wide variety of medication containers. Examples of medication containers include: a pre-filled or empty needle-less syringe having a fluid outlet at a tip of the syringe, a vial having a fluid outlet corresponding to the stopper at the vial closure, a bag containing a premixed solution having a Luer fitting connector or an IV set spikeable port, an envelope (e.g., disposable, rigid, semi-rigid or flexible envelope, etc.) having an integral Luer fitting or tubing extended therefrom, a fluid transfer device used with medication vials having a luer fitting connector, and/or a fluid delivery tubing set having an integral luer fitting at one end of the tubing.

The medication code source 6 can be/include any one or more of a barcode (one or two dimensional), an optical image (e.g. picture, symbol, image, hologram, etc.), an NDC code (National Drug Code), a segment of the NDC code identifying the drug product, a segment of the NDC code identifying the drug package, a unique identifier code, human readable code, a machine readable code, a manually entered code or other codes that can be created to uniquely identify one or more of a medication's name, manufacturer, re-packager, distributer, strength (concentration), dosage form, dose instructions (whether generic for all patients or specifically prescribed for a particular patient), formulation, package form, package size, contained volume, package serial number, lot number, expiration date.

Additional complementary information can also be included within the medication code source 6 such as a reference to a database or document (via, for example, a URL, etc.) which can include additional information regarding the medication such as how it interacts with other medications and/or information regarding medications that are often administered along with the specified medication. As an example, before and/or coincident to the medication being administered, such complementary information may be accessed by a reader (whether at the point of administration or otherwise) so that additional information can be presented regarding the medication (including which medications should not be administered concurrently). In addition, in some implementations, it can be determined whether there is a possibility of an adverse reaction if the medication is delivered (whether via overmedication or interaction with previously delivered medications or due to some potential patient adverse condition). Such complementary information can also identify other medications that are often administered with the identified medication (especially in the case of complex protocols).

During use, the operator of read-write instrument 4 first determines which medication code source 6 is to be used and positions it in range of reader 10. Alternately, the operator can manually enter medication code source 6 information by using user interface 26. Secondly, the operator positions target 8 in range of writer 16. This positioning of target 8 may be a manual process or facilitated by automated equipment. The scanner element 12 of the reader 10 reads medication code source 6 and produces read information 14. Instrument control 24 receives read information 14 and prepares for a writing operation. Writer 16 receives read information 14 from instrument control 24 and writing element 18 of the writer 16 produces written information 20 to be written or deposited on target 8's fluid outlet 22. Writing element 18 can be one of a laser writer, a hot stamp, a printer, a magnetic encoder, an electronic data packet message, or a surface treatment facilitating optical, magnetic, electronic or proximity recognition. Once written, target 8 is encoded with information from medication code source 6.

As a first alternative, the writer 16 can deposit the encoded information on an adhesive backed element which can then be applied to target 8 (e.g., an RFID tag or other machine readable label applied to target). As a second alternative, writer 16 may apply a coded article such as a coded ring to target 8. As a third alternative the coded information or article can be radially written on the syringe surface 50 or take the form of coded disc 52 applied to surface 50.

Figure 1B:
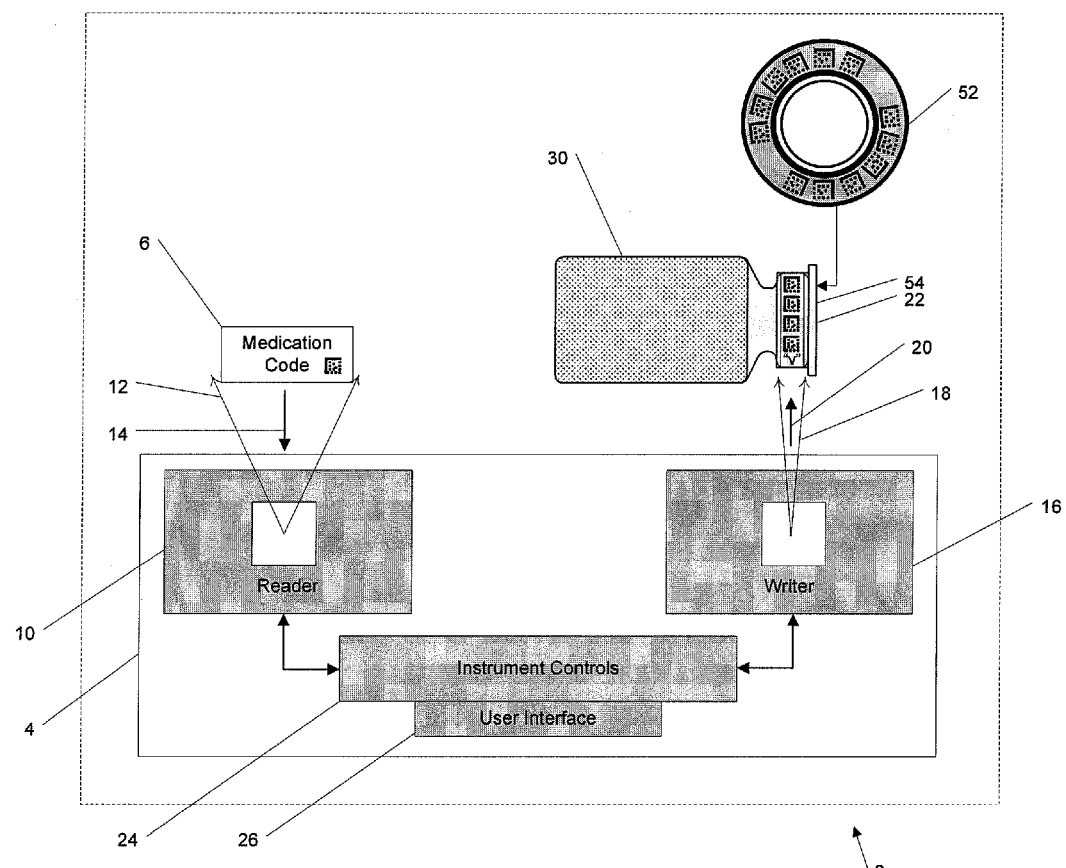
FIG. 1B is a diagram illustrating a medication identification information read and write apparatus for use with a vial container.

FIG. 1B is a diagram illustrating a medication identification information read and write apparatus 2 for use with a vial. Similar to FIG. 1A, apparatus 2 can include a read-write instrument 4 that can include one or more information readers 10, an information writer 16 and an information target 30. With such an arrangement, an entity or device such as a pharmaceutical manufacturer, local pharmacy or in-hospital pharmacy can access or read medication identification information 14 from medication code source 6. This read medication identification information 14 can be subsequently written, deposited or encoded in the form of medication identification information 20 onto or into information target 30 for the purpose of encoding target 30 at the fluid outlet (vial septum, stopper or stopper closure).

Similar to FIG. 1A, additional complementary information can also be included within the medication code source 6 such as a reference to a database or document (via, for example, a URL, etc.) which can include additional information regarding the medication such as how it interacts with other medications and/or information regarding medications that are often administered along with the specified medication.

As a first alternative, the writer 16 can deposit the encoded information on an adhesive backed element which can then be applied to target 30 (e.g., an RFID tag or other machine readable label applied to target). As a second alternative, writer 16 may apply a coded article such as a coded disk 52 to target 30. As a third alternative the coded information or article can be radially written on the vial surface 54 in a pattern similar to disc 52.

Figure 2:
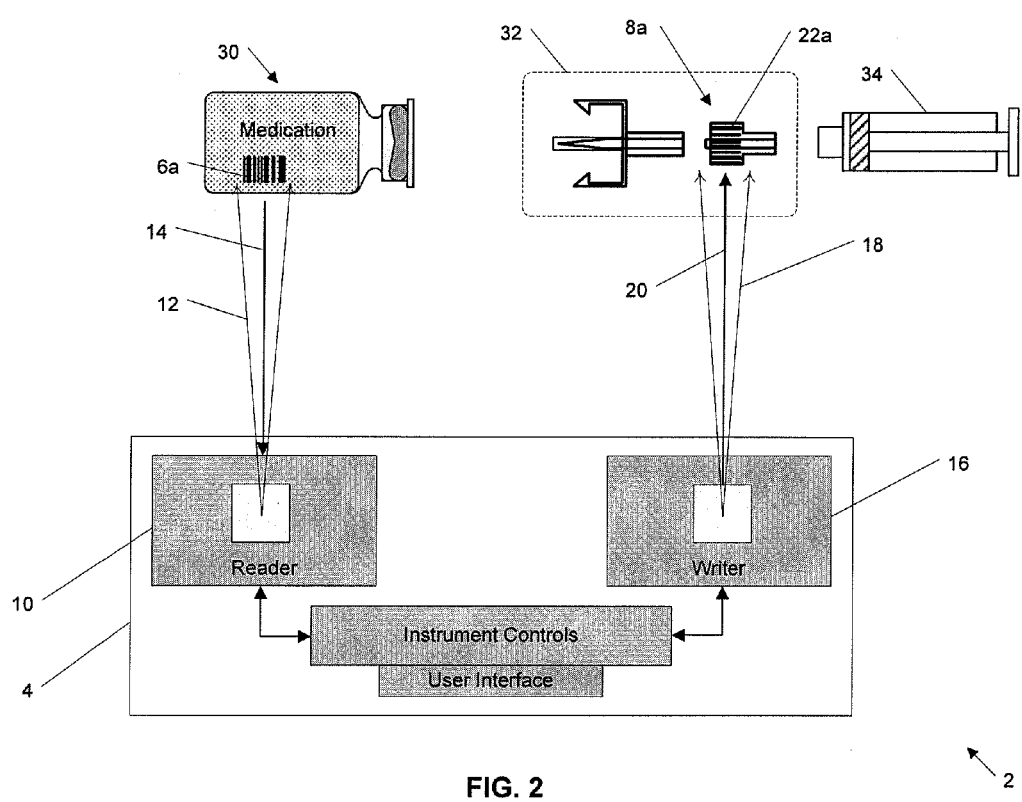
FIG. 2 is a diagram illustrating an alternate medication identification information read and write apparatus of FIG. 1.

FIG. 2 is a diagram illustrating an alternative medication identification information read and write apparatus. In this variation, the scanner element 12 of reader 10 reads medication code source 6a from vial 30 and produces read information 14. Instrument control 24 receives read information 14 and prepares for a writing operation. Writer 16 receives read information 14 from instrument control 24 and the writing element 18 of writer 16 produces written information 20 to be written or deposited on target 8a's fluid outlet 22a. Writing element 18 can be one of a laser writer, a printer, a magnetic encoder, an electronic data packet message, or a surface treatment facilitating optical, optical image, magnetic, electronic or proximity recognition. Once written, target 8a is encoded with medication code source 6a's information. In this variation, target 8a is part of vial adapter and ID transfer element 32 designed for use with empty container 34 (shown here as a syringe) for the withdrawal and transfer of medication to a patient. As an alternative, the writer can deposit the encoded information on a adhesive backed element which can then be applied to target 8a. As a second alternative, writer 16 may apply a coded article such as a coded plastic ring to target 8a.

Other variations of medication containers and information targets can be incorporated that use various forms of medication code source 6a to provide information about the contents of the container and different target 8a with alternate fluid outlet 22a configurations. Targets can be encoded as separate parts and then grouped with other parts as assemblies.

The apparatus and process depicted in FIG. 2 customizes medication vial 30 to improve accuracy and safety of medication delivery. Vial 30 can be customized to be utilized by a self-auditing medication delivery system including a fluid input (not shown) that is coupled to a patient. During medication delivery to a patient, fluid outlet 22a is coupled to container 34 (e.g., a syringe). Fluid outlet 22a can be coupled to a fluid input (not shown) and then medication within container 34 is dispensed through fluid outlet 22a and into the fluid input. The fluid input (not shown) includes a reading device that reads encoded information 20 from fluid outlet 22a and can then utilize the information 20 to verify that a type and quantity of medication delivered by container 34 is proper for the patient. Thus, the current subject matter provides an advantageous way of customizing medication containers to enable a verification of proper medication delivery.

In a further implementation, vial 30 can be customized to provide a particular dosage of medication for a patient. Container 34 may be configured to hold a fraction of the entire volume of medication held in medication vial 30 as will be discussed later regarding FIG. 7. Information 20 may include information that is indicative of a dosage to be delivered to the patient from container 34. Such an implementation is advantageous in that it allows customization of medication to enable dosing to a particular patient without error. One example of such customization may be providing a dose for pediatrics or for a patient of a given weight class. In another variation, container 34 may be a "multi-dose" syringe configured to hold multiple doses of medication from vial 30. In yet further variations, medication in container 34 may be diluted and information 20 may additionally be indicative of dilution parameters. In yet further variations, medication in container 34 may be divided into multiple sub-container targets and repackaged by a pharmacy as will be discussed later.

Figure 3:
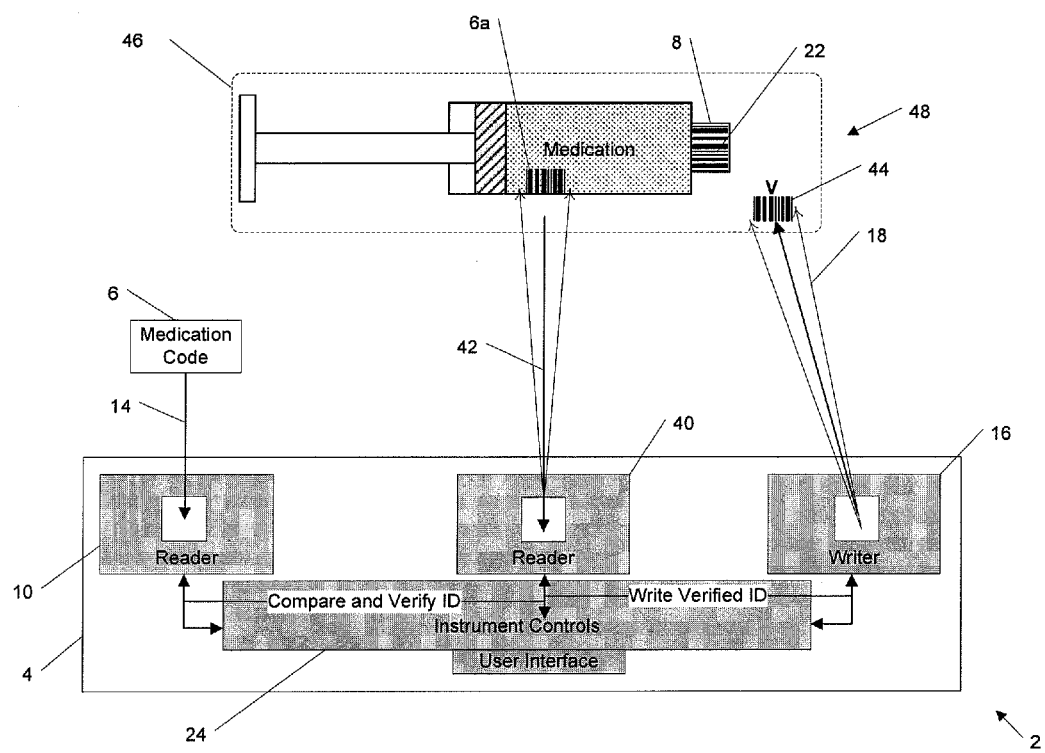
FIG. 3 is a diagram illustrating an identification information read, write and verification apparatus.
Figure 4:
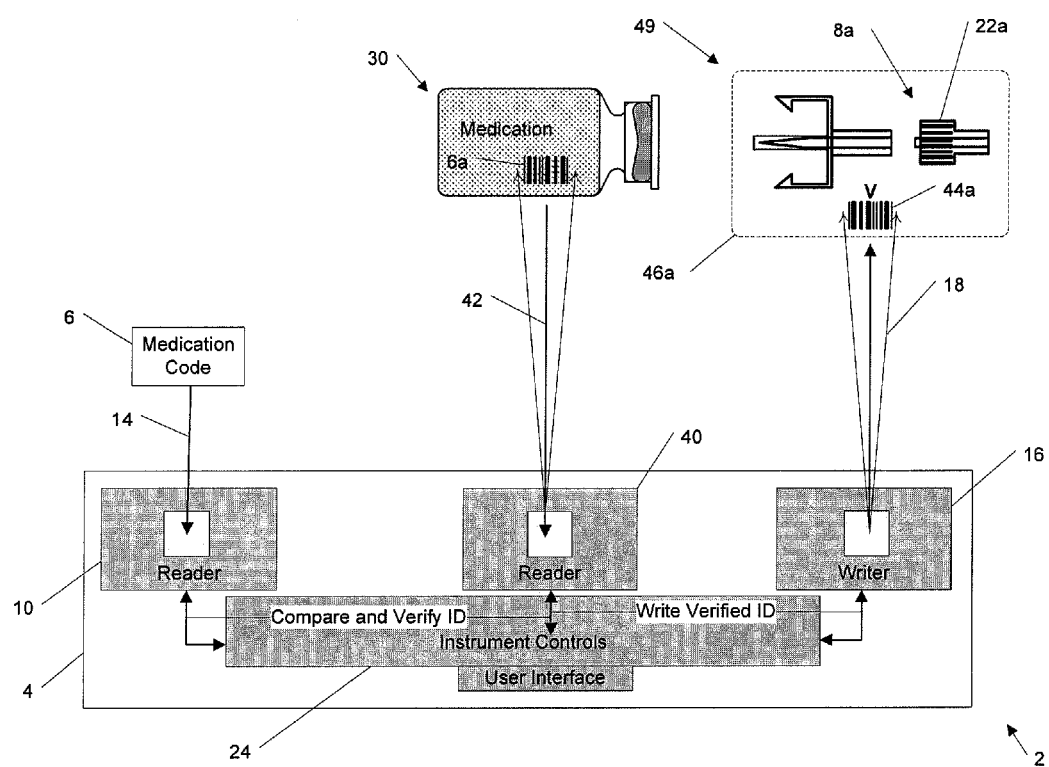
FIG. 4 is a diagram illustrating an alternate identification information read, write and verification apparatus of FIG. 3.
Figure 5:
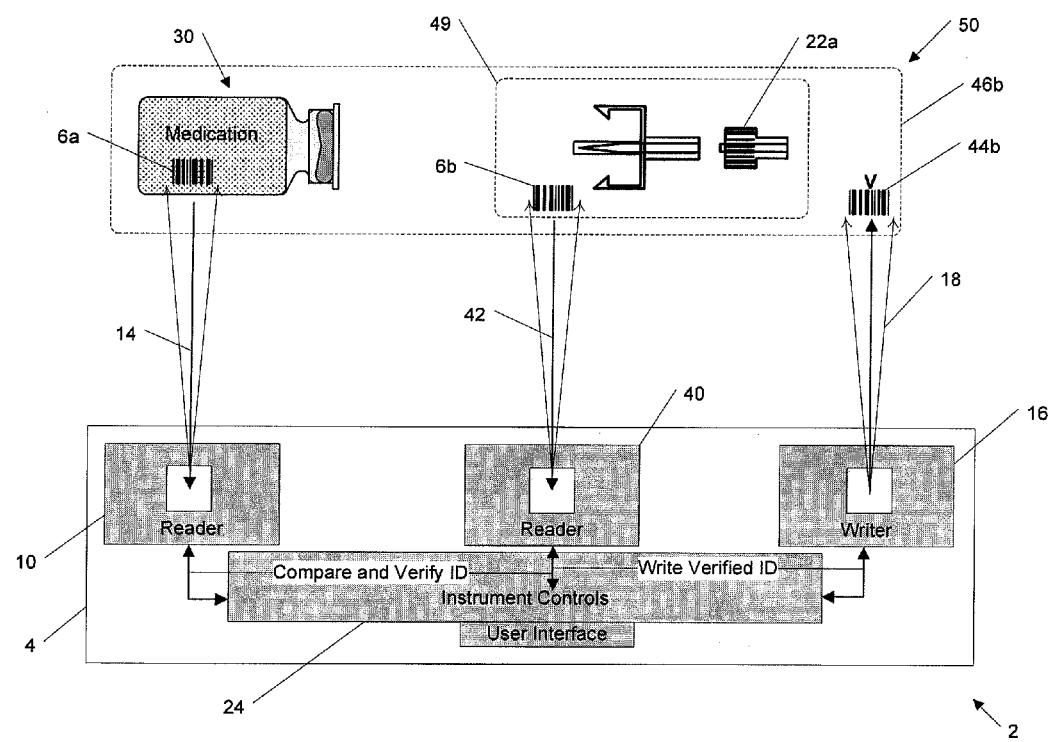
FIG. 5 is a diagram illustrating a second alternate identification information read, write and verification apparatus of FIG. 3.

FIGS. 3, 4 and 5 illustrate arrangements to read encoded medication information from various medication code sources and encoded targets and to verify their identity and write identifying information on packaging. FIG. 3 illustrates a first variation of apparatus 2 wherein the medication container is a prefilled or empty syringe. In this case medication code source 6 is read by reader 10 providing a desired identification. A second reader 40 (or a second read operation/position of first reader 10) can scan medication code source 6a and produces read information 42. Instrument control 24 compares information 14 to information 42 and verifies that their identity matches. Writer 16 receives information 42 from instrument control 24 and writing element 18 writes information 44 onto package 46. A human readable indication of the verification, "V", can be part of written information 44. Package 46 can be a box, envelope, pouch or other medical product packaging forming fully packaged and labeled syringe 48. Alternately, reader 10 can scan medication code 6a instead of medication code 6 and reader 40 can scan encoded information 22 instead of medication code source 6a. Here, instrument control 24 compares medication code 6a to information 22 and verifies identity before writing information 44.

FIG. 4 describes a second variation of apparatus 2 wherein the medication container is vial 30 to be used with vial adapter and transfer apparatus 49. In this case medication code source 6 is read by reader 10 providing a desired identification. A second reader 40 (or a second read operation/position of first reader 10) scans medication code source 6a and produces read information 42. Instrument control 24 compares information 14 to information 42 and verifies their identity. Writer 16 receives information 42 from instrument control 24 and writing element 18 writes information 44a onto package 46a. A human readable indication of the verification, "V", can be part of written information 44a. Package 46a can be a box, envelope, pouch or other medical product packaging forming fully packaged vial adapter and transfer apparatus 49. Alternately, reader 10 can scan medication code 6a instead of medication code 6 and reader 40 can scan encoded information 22a instead of medication code source 6a. Here, instrument control 24 compares medication code 6a to information 22a and verifies identity before writing information 44a.

FIG. 5 is a third variation of apparatus and method 2 wherein the medication container is vial 30 to be used with vial adapter and transfer apparatus 49. In this case medication code source 6a is read by reader 10 providing a desired identification. A second reader 40 (or a second read operation/position of first reader 10) scans medication code source 6b and produces read information 42. Instrument control 24 compares information 14 to information 42 and verifies their identity. Writer 16 receives information 42 from instrument control 24 and writing element 18 writes information 44b onto package 50. A human readable indication of the verification, "V", can be part of written information 44b. Package 50 can be a box, envelope, pouch or other medical product packaging forming fully packaged vial 30 and vial adapter and transfer apparatus 49. Alternately, reader 40 can scan information 22a instead of medication code 6b. Here, instrument' control 24 compares medication code 6a to information 22a and verifies identity before writing information 44b.

Figure 6:
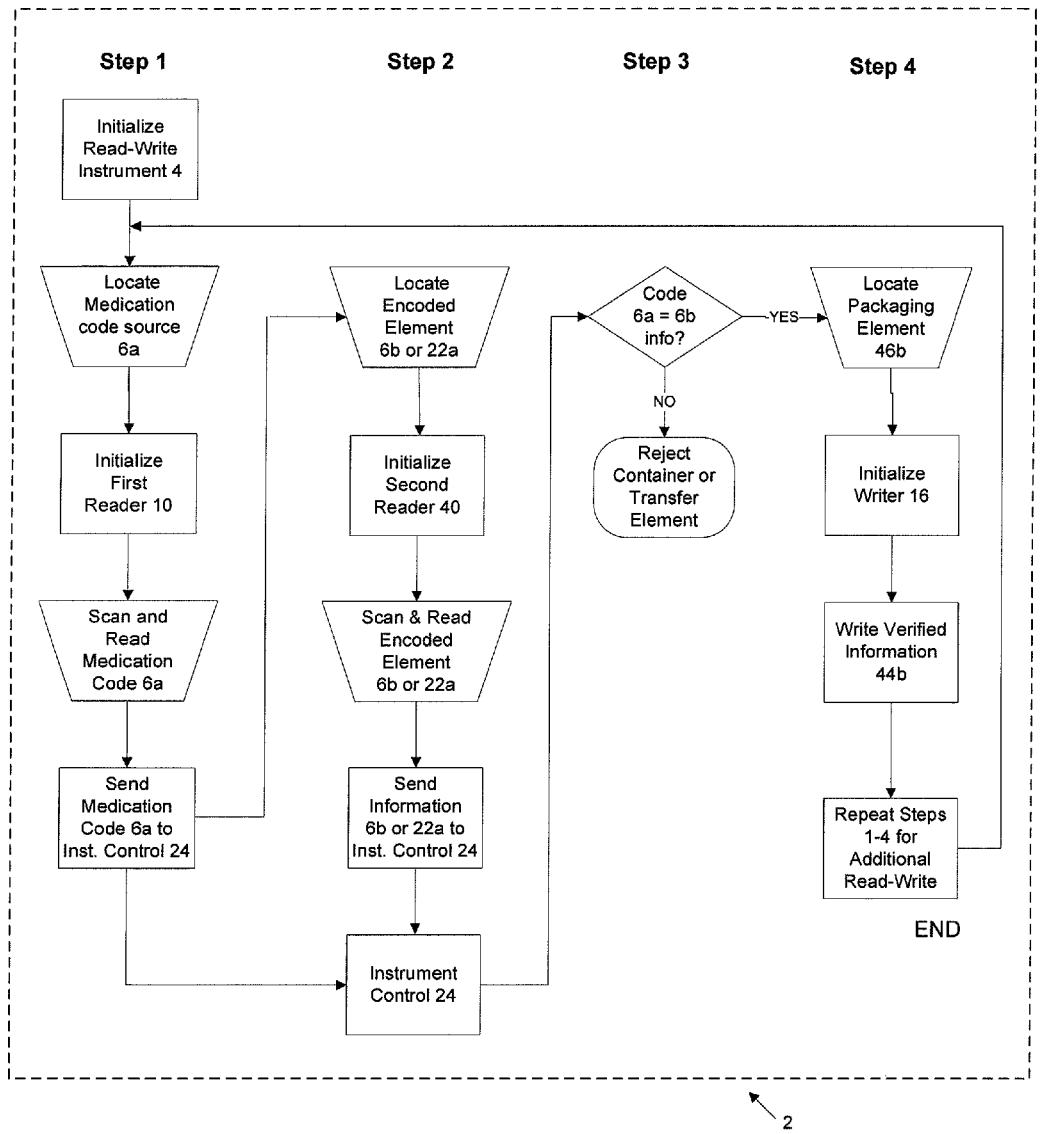
FIG. 6 is a flow diagram illustrating a sequence of steps describing a method and use of an apparatus such as the one in FIG. 5.

FIG. 6 is a process flow diagram relating to the use of a medication identification encoding and verification apparatus 2 such as is shown in FIG. 5.

Step 1—Initialize instrument 4, locate medication code source 6a, initialize first reader 10; locate, scan and read medication code source 6a, and send medication code 6a to instrument control 24.

Step 2—Locate encoded element 6b or 22a, initialize second reader 40, scan and read encoded element, and send information to instrument control 24.

Step 3—Compare first read information (e.g., medication code 6a) to second read information (encoded element 6b or 22a) and verify information identity. Reject container or transfer element if there is not a match.

Step 4—Locate packaging element 46b, initialize writer 16, write verified information 44b, and repeat from step 1 thru step 4 if needed/desired.

Figure 7:
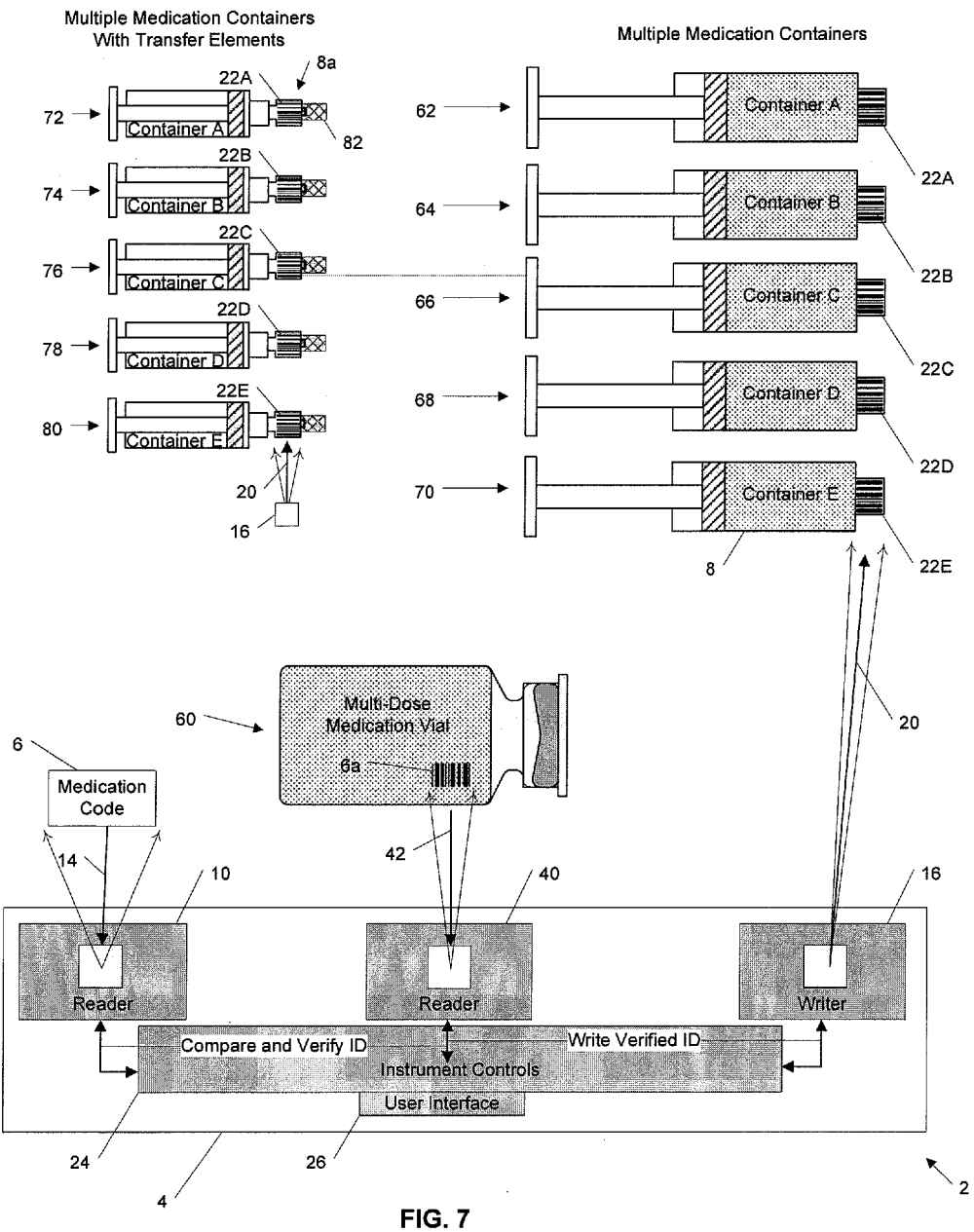
FIG. 7 is a diagram illustrating a third alternate identification information read, write and verification apparatus of FIG. 3.

FIG. 7 is a diagram illustrating a fourth variation medication identification information read-write and verification apparatus and method. This variation can be used in a pharmacy to read information from multi-dose medication container 60 and write information 20 onto multiple medication containers 62, 64, 66, 68, 70 (or onto multiple medication transfer elements 8a with cap 82 and attached to medication containers 72, 74, 76, 78, 80 as shown in the upper left). Encoded information 22A, 22B, 22C, 22D, and 22E can be written multiple times onto multiple containers 62, 64, 66, 68, 70 (or transfer elements 72, 74, 76, 78, 80) respectively. Any number of multiple doses and multiple medication containers can be used; there are five containers (A-E) shown in this example. The written information 20 can be the same for each medication container or it can be different. When different, the pharmacy operator can use user interface 26 to customize information 20 which can contain the same or different dose amounts (dose volume, concentration, etc.), different patient identifiers, different serial numbers, etc. In multi-dose container 60 arrangements, the reader 40 and/or instrument controls 24 can record the amounts introduced into each medication container 62-70 (or 72-80) and/or the amount remaining in the multi-dose medication container 60. This recorded information can be used for pharmacy records.

The method and apparatus of FIG. 7 depicts customization of medication container 60 for dosages that are smaller than the amount of medication held in medication container 60. This customization can provide a convenience to a caregiver and avoids error. A fluid receiving port (not shown here but can be seen in FIG. 10) coupled to a patient includes a reader that is configured to read the information 22 to verify and record a proper dose as being provided to a patient. The method and apparatus depicted in FIG. 7 along with the fluid receiving port connected to a patient and medication container coded fluid outlet reader provides an effective combination of dosage customization and electronic auditing to prevent error and to provide an automated form of electronic record keeping. The encoded information 20 on the target can be positioned such that it can be read by a medication administration device (fluid receiving port) when administering the medication to a patient without deliberate effort or work flow interruption on behalf of a clinician to facilitate information transfer between the medication container and the medication administration device.

Figure 8:
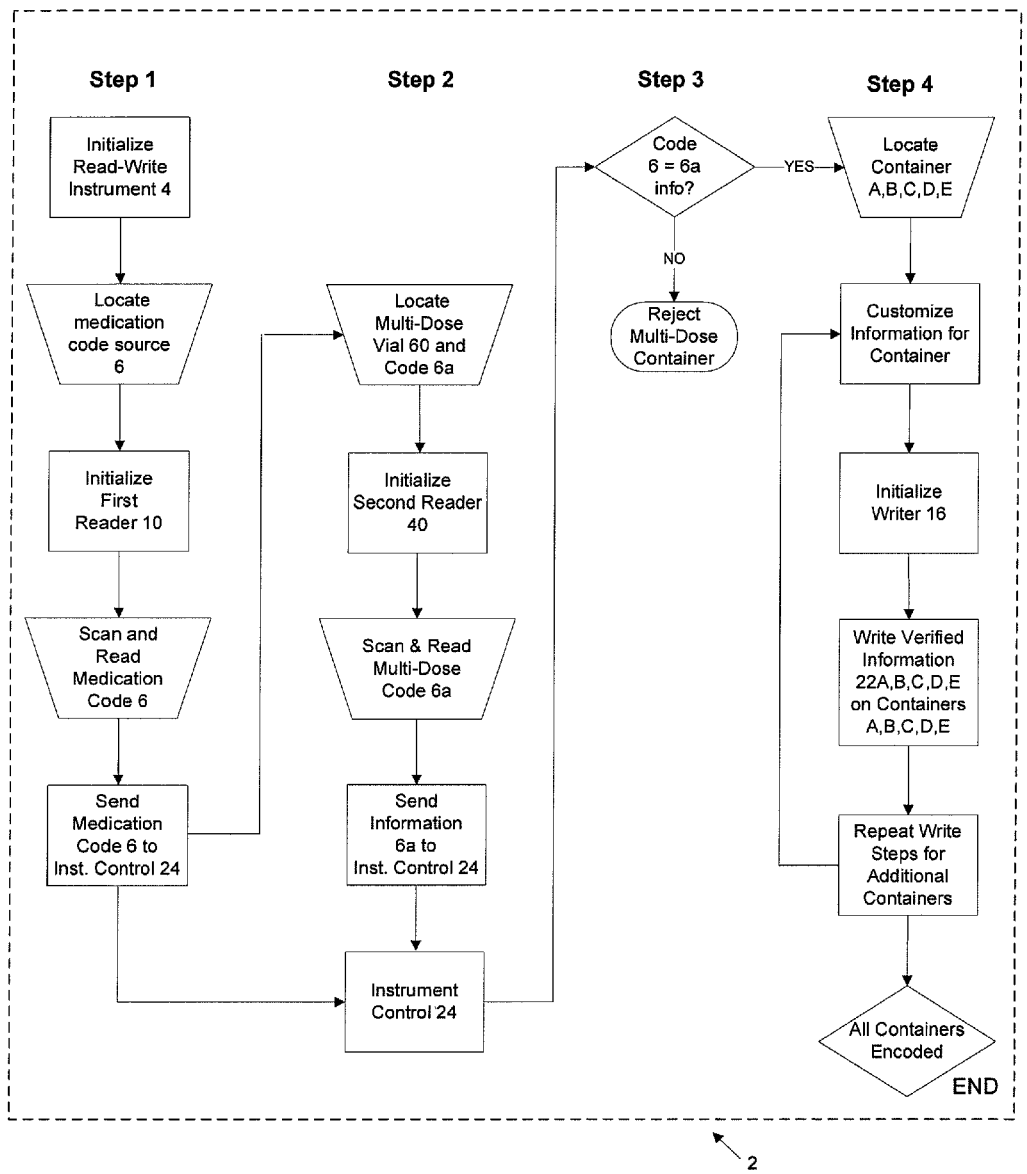
FIG. 8 is a flow diagram illustrating a sequence of steps describing a method and use of an apparatus such as the one in FIG. 7.

FIG. 8 is a process flow diagram relating to the use of a medication identification encoding and verification apparatus 2 such as is shown in FIG. 7.

Step 1—Initialize instrument 4, locate medication code source 6, initialize first reader 10, locate, scan and read medication code source 6, and send medication code 6 to instrument control 24.

Step 2—Locate multi-dose vial 60, initialize second reader 40, scan and read multi-dose code 6a, and send information to instrument control 24.

Step 3—Compare first read information (e.g., medication code 6a) to second read information (code 6a) and verify information identity. Reject multi-dose container if there is not a match.

Step 4—Locate medication container, customize information 20 as required, initialize writer 16, write information 22A, and repeat from steps for additional containers B-E and information 22B-E as needed/desired. When all containers are encoded, END the process.

Figure 9:
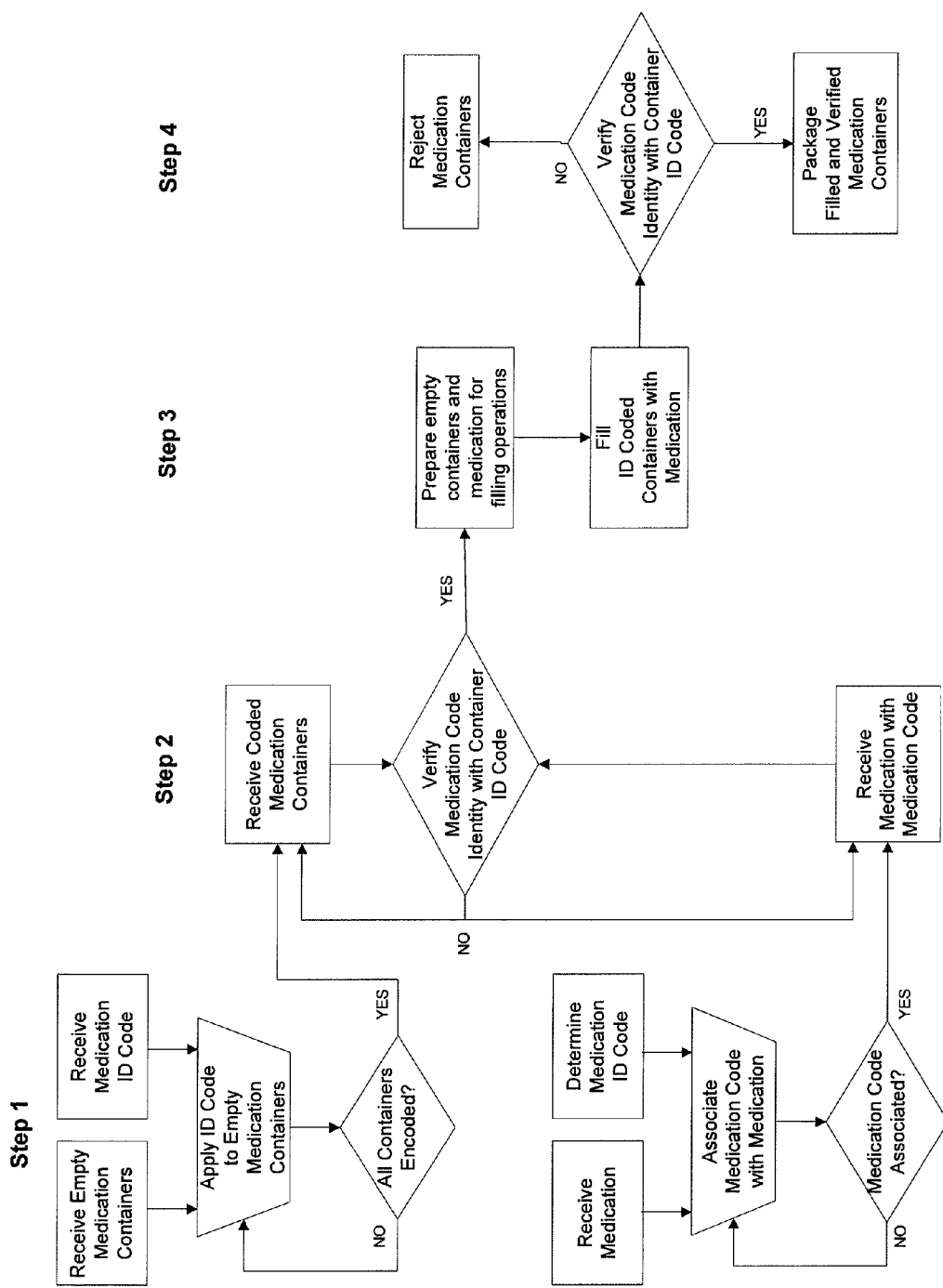
FIG. 9 is an alternate flow diagram illustrating a sequence of steps describing a method and use of an apparatus such as the one in FIG. 1.

FIG. 9 is an alternate process flow diagram to that shown in FIG. 6 relating to the use of a medication identification encoding and verification system 2 such as is shown in FIG. 1. The process can be organized in any number of sequential or parallel steps to accomplish the read ID Code and write ID Code method. One such process is described showing the application of the ID Code to an empty container before a medication is filled into the container. Other process variations can be envisioned that fill the medication into the container before the ID Code is written onto the container (not shown).

Step 1—Prepare empty containers by application of encoded information element and prepare medication for container filling. Empty medication containers are received and inspected for use. Identification ID Code element is received and prepared for application. The ID Code element is written (applied) to the empty container (syringe, vial, bag, etc.). Medication is received and the medication ID Code determined. The ID Code is associated with the medication.

Step 2—Empty encoded containers and coded medication are delivered to an assembly operation. Prior to filling the empty containers with medication, the identity of the medication ID Code can be verified to determine if the ID Code on the empty container is the same as that associated with the medication. If they are the same, proceed to the filling operation. Each and every medication container can be verified or a lot sample can be verified.

Step 3—Empty encoded containers and coded medication are prepared for the filling process. Medication is filled into the empty containers.

Step 4—After filling the empty containers with medication, the identity of the medication ID Code can be verified to determine if the ID Code on the filled container is the same as that associated with the medication. If the identity is the same, proceed to the packaging operation. If there is not identity, the filled containers are rejected.

Figure 10:
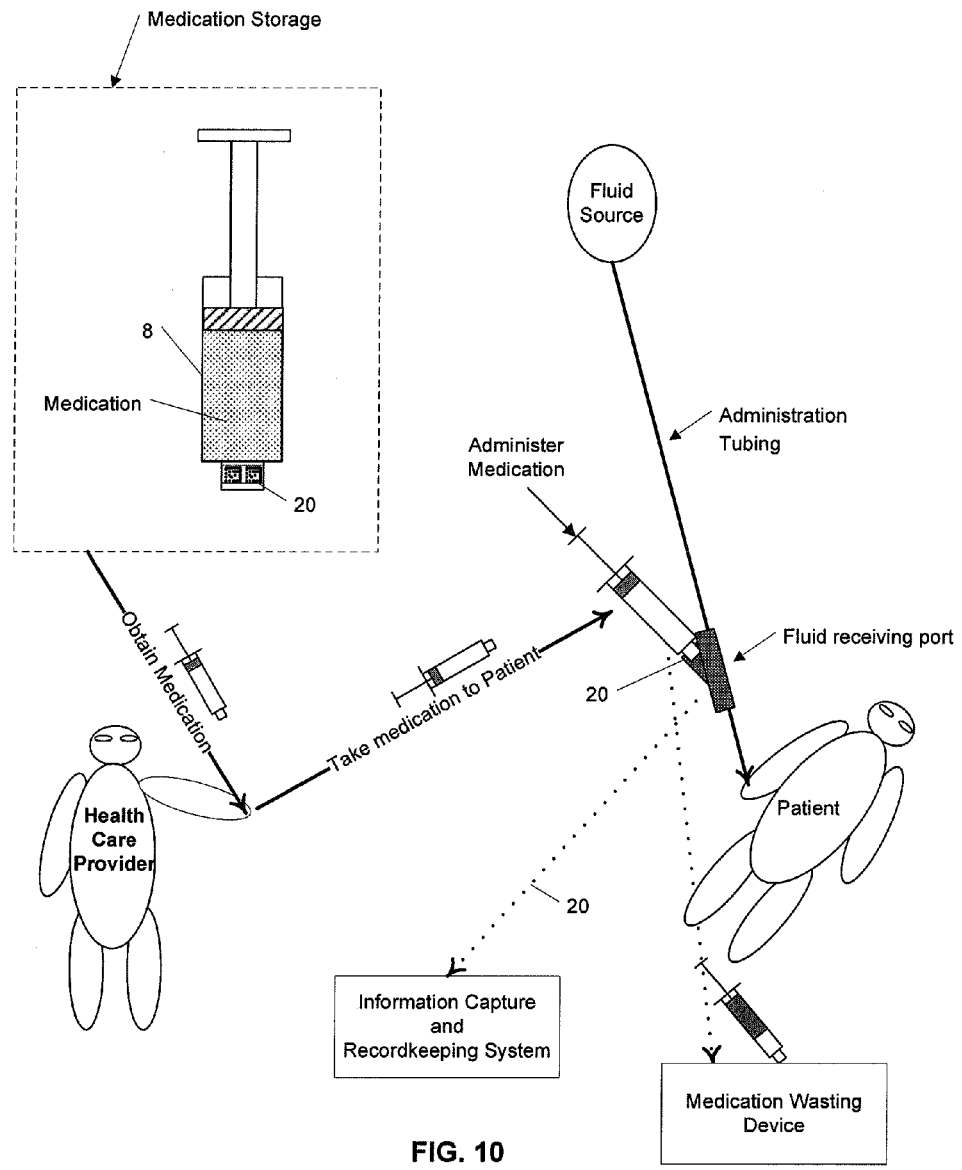
FIG. 10 is a diagram illustrating a sequence of steps a caregiver would use in the administration of medication to a patient.

FIG. 10 illustrates caregiver workflow for administration of medication from the encoded medication container 8. A patient is receiving fluid delivery through an administration tubing set. A fluid receiving port for medications is attached to the administration tubing close to the patient. During execution of medication delivery, a health care provider obtains a medication container 8 from storage (medication dispensing unit, medication cart, medication kit, etc.). The health care provider takes the medication to the patient and inserts the medication container into the fluid receiving port. Upon attachment the fluid receiving port identifies the medication ID code 20 and transmits the information to an Information Capture and Recordkeeping System. The health care provider then administers the medication to the patient and the medication information encoded within the label is transmitted to the Information Capture and Recordkeeping System, time stamped and recorded. In addition, in some implementations, remaining medication is wasted/disposed in a Medication Wasting Device which can read the medication ID code 20 when the medication container 8 is coupled thereto.

Figure 11:
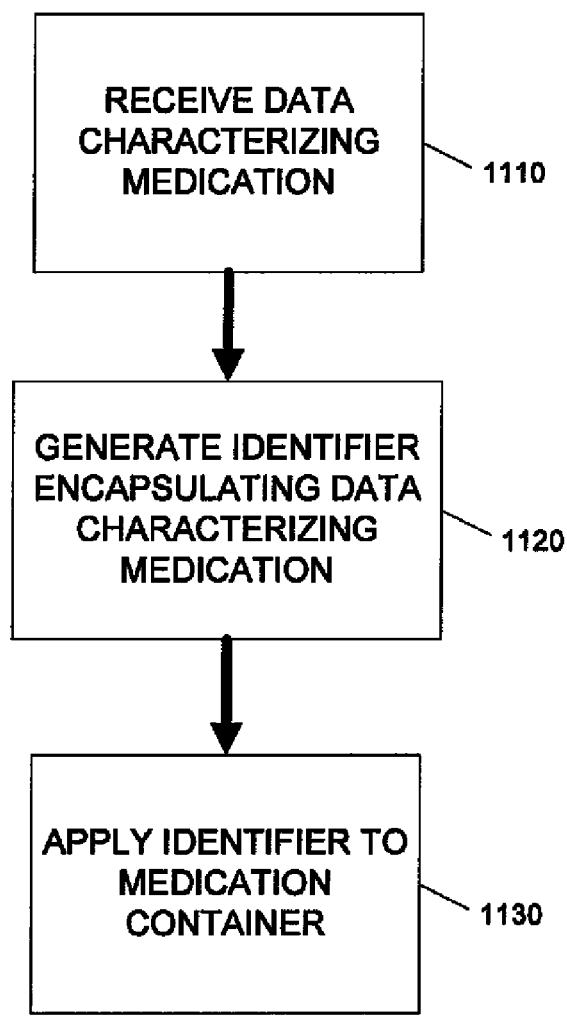
FIG. 11 is a process flow diagram illustrating generation and application of an identifier to a medication container.

FIG. 11 is a process flow diagram illustrating a method 1100 in which, at 1110, data characterizing medication within a medication container is received. Thereafter, at 1120, an identifier encapsulating data characterizing the medication is generated. This identifier is applied, at 1130, to medication container and is positioned such that it is automatically readable by a medication administration device when administering the medication to a patient and/or automatically readable by a medication wasting device when the medication is disposed therein (i.e., the identifier is read without deliberate effort on behalf of a clinician administering the medication to facilitate information transfer between the medication container and the medication administration device).

Features and functions of a sample medication container encoded fluid outlet and the use of same by a medication injection site/medication administration device are detailed in the U.S. patent application Ser. Nos. 12/614,276, 12/765,707, and 12/938,300 all entitled "MEDICATION INJECTION SITE AND DATA COLLECTION SYSTEM". Features and functions of a sample vial adapter and encoded fluid transfer element are detailed in U.S. patent application Ser. No. 12/768,509 entitled "MEDICATION AND IDENTIFICATION INFORMATION TRANSFER APPARATUS". The contents of each of the aforementioned applications are hereby fully incorporated by reference. Other medication containers and/or vial adapters and fluid transfer elements may be implemented with this read-write encoding system.

In addition, while the foregoing examples are mainly directed to the preparation and administration of medication within medication containers, it will be appreciated that the same concepts can be applied to a medication wasting device. For example, a medication wasting device can be configured to receive a syringe containing a controlled substance and bearing an identifier such that the identifier is automatically read by the medication wasting device when the syringe is coupled thereto. One example of a medication wasting device is described in U.S. Pat. App. Ser. No. 61/358,937 entitled: "Medication Waste Collection Apparatus", the contents of which are hereby fully incorporated by reference.

The subject matter described herein may be embodied in systems, apparatus, methods, and/or articles depending on the desired configuration. In particular, aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, applications, components, or code) include machine instructions for a programmable processor, and may be implemented in a high-level procedural and/or object-oriented programming language, and/or in assembly/machine language. As used herein, the term "machine-readable medium" refers to any tangible/non-transitory computer program product, apparatus and/or device (e.g., magnetic discs, optical disks, memory, Programmable Logic Devices (PLDs)) used to provide machine instructions and/or data to a programmable processor.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the following claims.

What is claimed is:

1. A method comprising:
   receiving data characterizing medication within or to be placed within a medication container, the medication container being a syringe comprising a barrel portion and a tip portion comprising a fluid outlet;
   electronically generating, using the received data, an optical identifier encapsulating data characterizing the medication; and
   applying the identifier to the tip portion of the medication container, the identifier being positioned such that it is automatically read by a medication administration device when the medication container is rotated while it is being fluidically coupled to the medication administration device;
   wherein the generating, and at least one of the receiving and applying is performed by a read and write apparatus.

2. A method as in claim 1, wherein the tip portion comprises a cylindrical or conical outer surface terminating at the fluid outlet and the identifier is applied to the outer surface.

3. A method as in claim 1, wherein the tip portion comprises a Luer fitting and the identifier is positioned on the Luer fitting.

4. A method as in claim 1, wherein the medication administration device comprises:
   a housing;
   a medication port accessible via an outer surface of the housing;
   an identification sensor disposed within the housing to generate information characterizing contents of the medication container when the fluid outlet of the medication container is fluidically coupled to the medication port; and
   a transmitter disposed within the housing and in communication with the identification sensor to transmit the information generated by the identification sensor to a remote data collection system.

5. A method as in claim 4, wherein the encapsulated data comprises a reference to data accessible via a communications network.

6. A method as in claim 5, wherein the reference to data accessible via a communications network comprises a Uniform Resource Locator, a pointer to a look-up table, a database path, or a file path.

7. A method as in claim 4, wherein the medication administration device further comprises a memory storing data corresponding to the encapsulated data which is accessed when the medication administration device reads the identifier.

8. A method as in claim 4, wherein the encapsulated data is formatted using an industry standard representation of the medication being characterized or a proprietary representation of the medication being characterized.

9. A method as in claim 4, wherein the referenced data accessible via a communications network comprises data selected from a group consisting of: an NDC code (National Drug Code), a segment of the NDC code identifying the drug product, a segment of the NDC code identifying the drug package, a unique identifier code, a human readable alphanumeric, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date.

10. A method as in claim 1, wherein the identifier data comprises data selected from a group consisting of: an NDC code (National Drug Code), a segment of the NDC code identifying the drug product, a segment of the NDC code identifying the drug package, a unique identifier code, a human readable alphanumeric, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date.

11. A method as in claim 1, wherein the identifier is etched on an outer surface of the medication container.

12. A method as in claim 1, wherein the identifier comprises a label applied to the medication container.

13. A method as in claim 1, wherein the identifier comprises a coded disc, or coded ring secured to the medication container.

14. A method as in claim 1, further comprising:
   bundling the medication container with at least one other item bearing a second identifier corresponding to the identifier; and
   verifying, after the bundling, that the identifier on the medication container corresponds to the second identifier on the at least one other item.

15. A method comprising:
   electronically reading data characterizing medication from a primary information source;
   generating, using the read data, an optical identifier encapsulating data characterizing the medication; and
   automatically applying the identifier to a tip portion of a medication container filled or to be filled with the medication, the medication container being a syringe with a barrel portion and a Luer fitting at the tip portion, the identifier being positioned such that it is automatically read by a medication administration device when the Luer fitting of the medication source rotatably mates with a complementary fitting on the medication administration device without deliberate effort on behalf of a clinician administering the medication to facilitate information transfer between the medication container and the medication administration device;
   wherein the generating, and at least one of the receiving and applying is performed by a read and write apparatus.

16. A method as in claim 15, wherein applying the identifier to a medication container is before the container is filled with the medication from the medication source.

17. A method as in claim 15, wherein the identifier is applied on or adjacent to the Luer fitting.

18. A method comprising:
   electronically receiving data characterizing medication within a manually administrable medication container having a barrel portion and a tip portion with a fluid outlet and a Luer fitting;
   generating, using the received data, at least one optical identifier encapsulating data characterizing the medication; and
   applying the at least one identifier to tip portion of the medication container such that it is automatically read by a manually administrable medication device when the medication container is being coupled to the manually administrable medication device using the Luer fitting;
   wherein the manually administratable medication device comprises:
   a housing;
   a medication port extending from an outer surface of the housing to couple to a fluid outlet of the medication container, the medication port being fluidically coupled to the patient such that medication received via the medication port is immediately administered to the patient, the medication port having a complementary Luer fitting to mate with the Luer fitting of the medication container;
   an identification sensor disposed within the housing to automatically generate information indicative of contents of the medication container during coupling of the fluid outlet of the medication container to the medication port; and
   a transmitter disposed within the housing and in communication with the identification sensor to wirelessly transmit the information generated by the identification sensor to a remote data collection system;
   wherein the generating, and at least one of the receiving and applying is performed by a read and write apparatus.

19. A method as in claim 18, wherein at least two identifiers are applied to the medication container.

* * * * *